(12) United States Patent
Li

(10) Patent No.: US 7,106,831 B2
(45) Date of Patent: Sep. 12, 2006

(54) X-RAY DIAPHRAGM, X-RAY IRRADIATOR, AND X-RAY APPARATUS

(75) Inventor: Yuqing Li, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/946,861

(22) Filed: Sep. 22, 2004

(65) Prior Publication Data

US 2005/0069088 A1    Mar. 31, 2005

(30) Foreign Application Priority Data

Sep. 29, 2003   (CN) ............................... 03 1 64890

(51) Int. Cl.
  *G21K 1/00* (2006.01)
(52) U.S. Cl. ...................................... 378/152; 378/121
(58) Field of Classification Search ................ 378/119, 378/121, 145, 147, 150, 152, 153; 250/505.1
See application file for complete search history.

(56) References Cited

U.S. PATENT DOCUMENTS 3,947,690 A * 3/1976 Peyser ........................ 378/153

| 4,752,947 A | 6/1988 | Telorack ...................... 378/152 |
| 5,086,444 A | 2/1992 | Bartmann .................... 378/152 |
| 5,260,984 A | 11/1993 | Horbaschek ................ 378/150 |
| 5,287,396 A | 2/1994 | Stegehuis .................. 378/98.2 |

FOREIGN PATENT DOCUMENTS

JP        04-267041        9/1992

* cited by examiner

*Primary Examiner*—Courtney Thomas
(74) *Attorney, Agent, or Firm*—Carl B. Horton, Esq.; Armstrong Teasdale LLP

(57) ABSTRACT

An X-ray diaphragm which forms a pyramidal X-ray beam with use of a simple construction includes four blades which are arranged in a surrounding relation to four sides so as to form a pyramidal X-ray beam with an X-ray focus as a vertex, the four blades having a structure such that the blades are fitted in one another in the form of parallel crosses at portions corresponding to four-corner edges of the pyramid. The blades have respective plural cross beams, the cross beams being formed such that adjacent cross beams are fitted in each other. The distance between mutually opposed blades is variable.

11 Claims, 2 Drawing Sheets

X-RAY DIAPHRAGM, X-RAY IRRADIATOR, AND X-RAY APPARATUS

CROSS REFERENCE TO RELATED APPLICATIONS

This application claims the benefit of Japanese Application No. 03164890.8 filed Sep. 29, 2003.

BACKGROUND OF THE INVENTION

The present invention relates to an X-ray diaphragm, an X-ray irradiator, and an X-ray apparatus. Particularly, the invention is concerned with an X-ray diaphragm for forming a pyramidal X-ray beam with an X-ray focus as a vertex, as well as an X-ray irradiator and an X-ray apparatus both equipped with such an X-ray diaphragm.

In an X-ray irradiator there is used an X-ray diaphragm for forming a pyramidal X-ray beam with an X-ray focus as a vertex. The X-ray diaphragm comprises a first diaphragm close to an X-ray tube and a second diaphragm remote from the X-ray tube. An aperture of the first diaphragm and that of the second diaphragm are set small and large, respectively, to form a pyramidal X-ray beam (for example, a patent literature 1).

[Patent Literature1] Japanese Published Unexamined Patent Application No. Hei 4-267041 (pp. 3 to 4, FIGS. 1 to 3)

The above X-ray irradiator using two diaphragms to form a pyramidal X-ray beam is required to interlock the two diaphragms in order to adjust the spread of X-ray beam, resulting in that the construction thereof becomes complicated.

SUMMARY OF THE INVENTION

Therefore, it is an object of the present invention to provide an X-ray diaphragm which forms a pyramidal X-ray beam with use of a simple construction, as well as an X-ray irradiator and an X-ray apparatus each equipped with such an X-ray diaphragm.

(1) The present invention in one aspect thereof for solving the above-mentioned problem resides in an X-ray diaphragm having four blades which are arranged in a surrounding relation to four sides so as to form a pyramidal X-ray beam with an X-ray focus as a vertex, wherein the four blades have such a structure that the blades are fitted in one another in the form of parallel crosses at portions corresponding to four-corner edges of the pyramid.

(2) The present invention in another aspect thereof for solving the above-mentioned problem resides in an X-ray irradiator comprising an X-ray tube, an X-ray diaphragm having four blades which are arranged in a surrounding relation to four sides so as to form a pyramidal X-ray beam with an X-ray focus as a vertex, and a collimator for collimating the X-ray beam formed by the X-ray diaphragm, wherein the four blades have such a structure that the blades are fitted in one another in the form of parallel crosses at portions corresponding to four-corner edges of the pyramid.

(3) The present invention in a further aspect thereof for solving the above-mentioned problem resides in an X-ray apparatus comprising an X-ray tube, an X-ray diaphragm having four blades which are arranged in a surrounding relation to four sides so as to form a pyramidal X-ray beam with an X-ray focus as a vertex, and a collimator for collimating the X-ray beam formed by the X-ray diaphragm and directing the collimated beam to an object to be radiographed, wherein as the X-ray diaphragm there is used the X-ray diaphragm described in any of claims 1 to 3.

According to the invention in the above aspects, the X-ray diaphragm has four blades which are arranged in a surrounding relation to four sides so as to form a pyramidal X-ray beam with an X-ray focus as a vertex, and the four blades have such a structure that the blades are fitted in one another in the form of parallel crosses at portions corresponding to four-corner edges of the pyramid. With such a simple construction it is possible to form a pyramidal X-ray beam.

From the standpoint of forming a pyramidal beam properly, it is preferable for the blades to have cross beams formed such that adjacent cross beams are fitted in each other. From the standpoint of making the widening of the pyramidal beam variable, it is preferable that the distance between the mutually opposed blades is variable.

From the standpoint of diminishing the area of a collimator blade it is preferable that the X-ray diaphragm be interlocked with the collimator. For rotating an irradiation field of the pyramidal beam in a plane parallel to an axis of the X-ray tube it is preferable that the X-ray diaphragm and the collimator be rotatable in a plane parallel to the axis of the X-ray tube.

According to the present invention, it is possible to provide an X-ray diaphragm which forms a pyramidal X-ray beam with use of a simple construction, as well as an X-ray irradiator and an X-ray apparatus each equipped with such an X-ray diaphragm.

Further objects and advantages of the present invention will be apparent from the following description of the preferred embodiments of the invention as illustrated in the accompanying drawings.

DETAILED DESCRIPTION OF THE INVENTION

Figure 1:
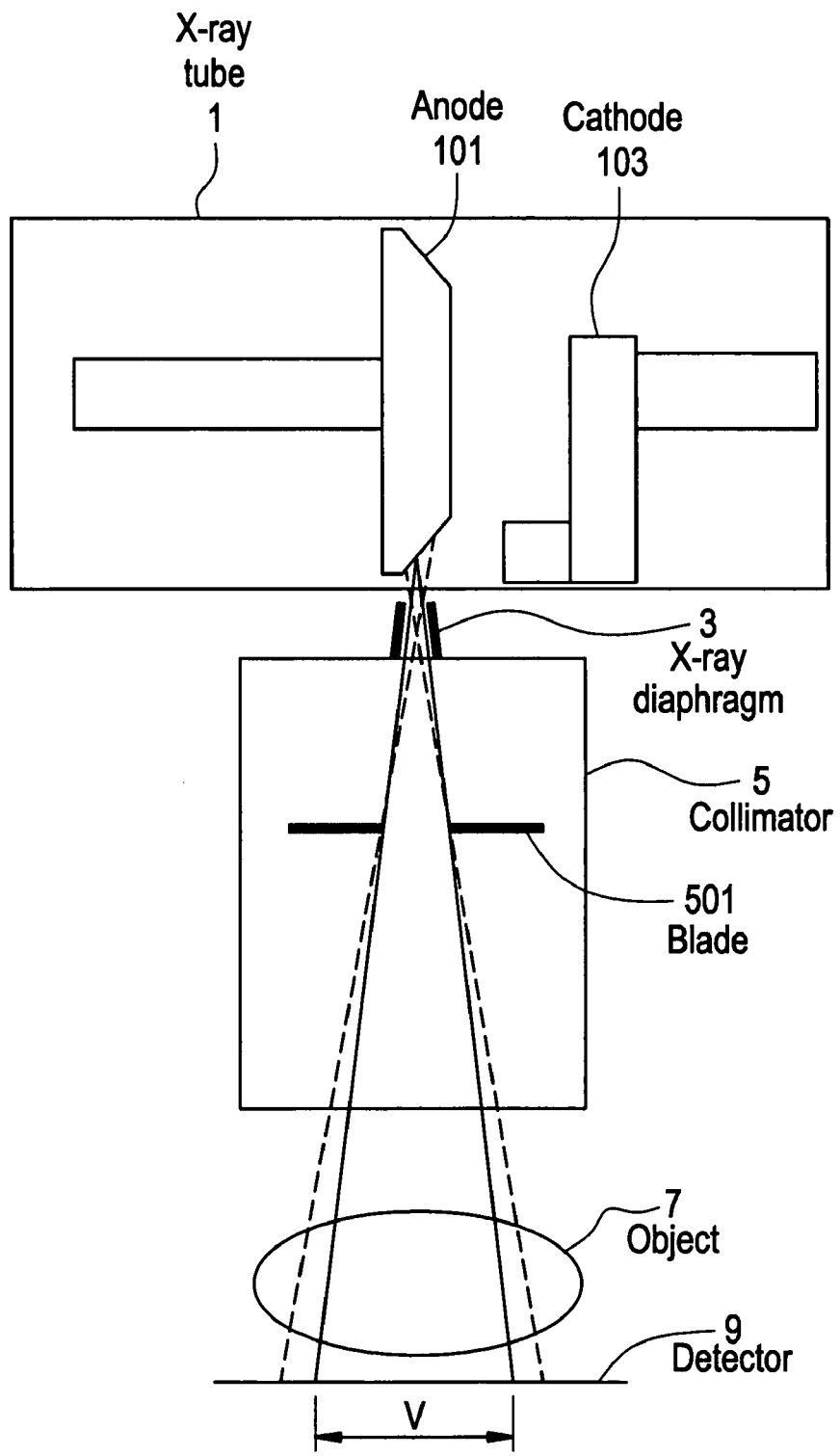
FIG. 1 illustrates a schematic construction of an X-ray irradiator.

An embodiment of the present invention will be described in detail hereinunder with reference to the accompanying drawings. FIG. 1 illustrates a schematic construction of an X-ray apparatus embodying the present invention. This apparatus is an example of a mode for carrying out the invention. With the construction of this apparatus there is shown an example of a mode for carrying out the invention related to the apparatus thereof.

In the X-ray apparatus, as shown in the same figure, X-ray generated from an X-ray tube 1 is diaphragmed by an X-ray diaphragm 3 and is collimated by a blade 501 disposed within a collimator 5, then the collimated X-ray is directed toward an object 7 to be radiographed, and the X-ray which has passed through the object 7 is detected by a detector 9.

The portion comprising the X-ray tube 1, X-ray diaphragm 3 and collimator 5 is an example of a mode for carrying out the invention with respect to the X-ray irradiator thereof. With the construction of this apparatus, there is shown an example of a mode for carrying out the invention with respect to the X-ray irradiator thereof.

The X-ray tube 1 is an example of a mode for carrying out the present invention with respect to the X-ray tube defined in the invention. The X-ray diaphragm 3 is an example of a mode for carrying out the invention with respect to the X-ray diaphragm thereof. The collimator 5 is an example of a mode for carrying out the invention with respect to the collimator defined in the invention.

The X-ray tube 1 has an anode 101 and a cathode 103, and X-ray is generated from a point of collision of electrons emitted from the cathode 103 anode 101.

The X-ray thus generated passes through the X-ray diaphragm 3 and the collimator 5 and is applied to the object. The X-ray diaphragm 3 is formed of an X-ray shielding material, e.g., lead. A blade 501 of the collimator 5 is also formed of such an X-ray shielding material, e.g., lead.

A visual field V of X-ray is determined by an aperture of the blade 501 in the collimator 5. The X-ray diaphragm 3 is formed so that the X-ray generated from the X-ray tube 1 forms a pyramidal beam with an X-ray focus on the anode 101 as a vertex, thereby diminishing the dose of X-ray generated from any other portion than the focus and spreading outside the irradiation field as indicated with broken lines.

The X-ray generated from any other portion than the focus is also called off-focal radiation. The off-focal radiation is conspicuous particularly in a direction perpendicular to the axis of the X-ray tube 1, i.e., in a direction perpendicular to the paper surface. Such an off-focal radiation is also diminished effectively by the X-ray diaphragm 3. The X-ray diaphragm 3 is also called an off-focal blade.

In the collimator 5, the aperture of the blade 501 is variable, whereby the irradiation field V of X-ray is adjusted. The diaphragming quantity of the X-ray diaphragm is also adjusted in interlock with adjustment of the aperture of the blade 501. More specifically, as the irradiation field V expands, the diaphragming quantity is decreased to increase the spread angle of the pyramidal beam, while as the irradiation field V contracts, the diaphragming quantity is increased to decrease the spread angle of the pyramidal beam.

By thus interlocking the aperture adjustment for the blade 501 and the diaphragming adjustment for the X-ray diaphragm 3 with each other it is possible to use a blade 501 of a small X-ray shielding area. This is for the following reason.

In case of adjusting the irradiation field by only the aperture adjustment for the blade 501, the diaphragming quantity of the X-ray diaphragm is fixed to a minimum value and the spread angle of the pyramidal beam is fixed to a value corresponding to a maximum irradiation field. Therefore, for obtaining a minimum irradiation field in such a condition, it is necessary to use a blade 501 of a large X-ray shielding area. However, this requirement is eliminated in the case where the spread angle of the pyramidal beam is changed by diaphragm adjustment which is conducted in accordance with the irradiation field.

The X-ray diaphragm 3 and the collimator 5 are rotatable integrally in a plane parallel to the axis of the X-ray tube 1, i.e., in a plane perpendicular to the paper surface, whereby the irradiation field of X-ray can be rotated in the plane parallel to the tube axis.

Figure 2:
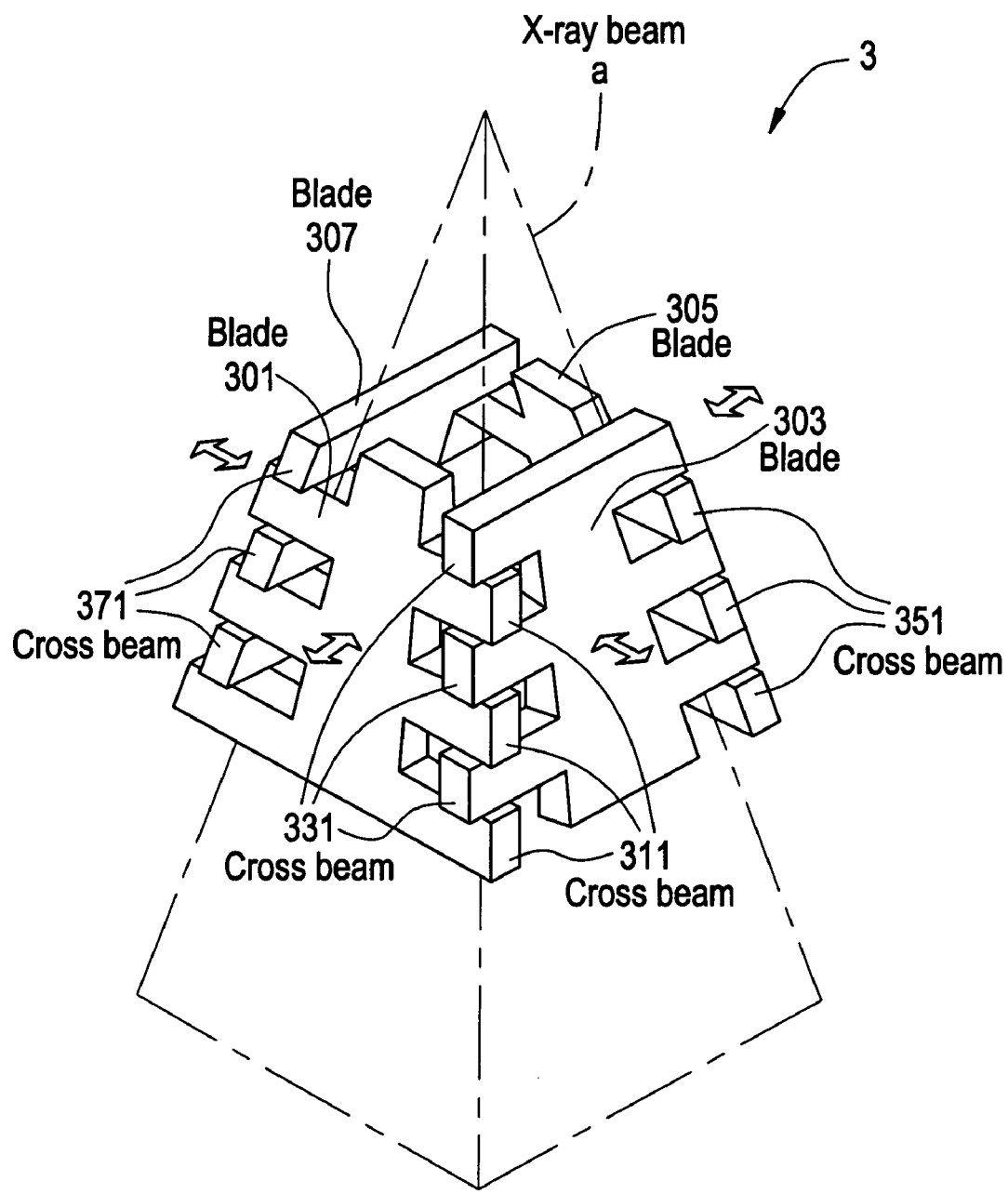
FIG. 2 illustrates an appearance of an X-ray diaphragm.

FIG. 2 illustrates the construction of the X-ray diaphragm 3. The X-ray diaphragm 3 is an example of a mode for carrying out the present invention. With the construction of this diaphragm, there is shown an example of a mode for carrying out the invention with respect to the X-ray diaphragm thereof.

As shown in the same figure, the X-ray diaphragm 3 is constituted by a combination of four blades 301, 303, 305, and 307, which are all flat structures. The blades 301, 303, 305, and 307 are each formed of an X-ray shielding material, e.g., lead, and have plural cross beams 311, 331, 351, and 371, respectively. In the illustrated example, the number of each of those cross beams is three, provided any other suitable number will do.

The four blades 301, 303, 305, and 307 are combined in a surrounding relation to four sides and in such a manner that adjacent cross beams are fitted in each other in the form of parallel crosses. Further, the four blades 301, 303, 305, and 307 are inclined so that upper ends of mutually opposed blades approach each other. As a result, the X-ray diaphragm 3 as a whole becomes a frame-like structure having an external form which is generally in the shape of a truncated pyramid.

By disposing such a frame-like structure in front of the X-ray tube 1 there is formed a pyramidal X-ray beam with an X-ray focus as a vertex, as indicated with dot-dash lines. The insides of the cross beams assembled in the form of parallel crosses correspond to four-corner edges of the pyramid. Since the parallel crosses are assembled by plural cross beams, it is possible to generate a pyramidal X-ray beam exactly.

In the X-ray diaphragm 3, by changing the distance of mutually opposed blades as indicated with arrows, the spread angle of X-ray beam in that direction is adjusted. Such an X-ray diaphragm is simplified in its construction because it does not employ such two interlocking diaphragms as in the prior art.

Besides, since the blades 301, 303, 305, and 307 are assembled in the form of parallel crosses using cross beams, there is no fear of X-ray leakage from the blade portions. Further, since the blades 301, 303, 305, and 307 are thick, there is no clearance between cross beams when seen from the X-ray tube 1 side, with no fear of X-ray leakage from between cross beams.

Therefore, even when the X-ray diaphragm 3 and the collimator 5 are rotated in a plane parallel to the axis of the X-ray tube 1 to turn the irradiation field of X-ray at an angle of, for example, 45° to 90°, the off-focal radiation can be diminished always in a satisfactory manner irrespective of the turning angle.

Many widely different embodiments of the invention may be configured without departing from the spirit and the scope of the present invention. It should be understood that the present invention is not limited to the specific embodiments described in the specification, except as defined in the appended claims.

The invention claimed is:

1. An X-ray diaphragm having four blades which are arranged in a surrounding relation to four sides so as to form a pyramidal X-ray beam with an X-ray focus as a vertex, the four blades having such a structure that the blades are fitted in one another in the form of parallel crosses at portions corresponding to four-corner edges of the pyramid, wherein one of the blades is configured to move from a first position parallel to a second position.

2. An X-ray diaphragm according to claim 1, wherein each of the blades has a plurality of cross beams, the cross beams of the blades being formed such that the adjacent cross beams are fitted in each other.

3. An X-ray diaphragm according to claim 1, wherein the distance between the mutually opposed blades is variable.

4. An X-ray diaphragm according to claim 1, wherein the diaphragm is configured to rotate.

5. An X-ray diaphragm according to claim 1, wherein the diaphragm is configured to rotate in a plane parallel to an axis of an X-ray tube.

6. An X-ray irradiator comprising:

an X-ray tube;

an X-ray diaphragm having four blades which are arranged in a surrounding relation to four sides so as to form a pyramidal X-ray beam with an X-ray focus as a vertex; and a collimator for collimating the X-ray beam formed by the X-ray diaphragm, the four blades having such a structure that the blades are fitted in one another in the form of parallel crosses at portions corresponding to four-corner edges of the pyramid, wherein one of the blades is configured to move from a first position parallel to a second position.

7. An X-ray irradiator according to claim 6, wherein each of the blades has a plurality of cross beams, the cross beams of the blades being formed such that the adjacent cross beams are fitted in each other.

8. An X-ray irradiator according to claim 6, wherein the distance between the mutually opposed blades is variable.

9. An X-ray irradiator according to claim 8, wherein the X-ray diaphragm is interlocked with the collimator.

10. An X-ray irradiator according to claim 6, wherein the X-ray diaphragm and the collimator are rotatable in a plane parallel to an axis of the X-ray tube.

11. An X-ray apparatus comprising:

an X-ray tube;

an X-ray diaphragm having four blades which are arranged in a surrounding relation to four sides so as to form a pyramidal X-ray beam with an X-ray focus as a vertex, wherein a first one of the blades is configured to fit with a second one of the blades, wherein the first one of the blades is conflaured to form a plurality of parallel crosses within the second one of the blades, wherein the parallel crosses are formed at an edge of a pyramid formed by the blades, and wherein the first one of the blades is configured to move from a first position parallel to a second position; and a collimator for collimating the X-ray beam formed by the X-ray diaphragm and directing the collimated beam to an object to be radiographed.

* * * * *

UNITED STATES PATENT AND TRADEMARK OFFICE
CERTIFICATE OF CORRECTION

| | | |
|---|---|---|
| PATENT NO. | : 7,106,831 B2 | Page 1 of 1 |
| APPLICATION NO. | : 10/946861 | |
| DATED | : September 12, 2006 | |
| INVENTOR(S) | : Li | |

It is certified that error appears in the above-identified patent and that said Letters Patent is hereby corrected as shown below:

In Claim 11, column 6, line 11, delete "conflaured" and insert therefor -- configured --.

Signed and Sealed this

Twenty-ninth Day of April, 2008

JON W. DUDAS
*Director of the United States Patent and Trademark Office*